United States Patent [19]

Erickson et al.

[11] 4,041,182
[45] Aug. 9, 1977

[54] BIO-PROTEIN FEED MANUFACTURING METHOD

[76] Inventors: Lennart G. Erickson, 1070 E. Meadow Circle, Palo Alto, Calif. 94303; Howard E. Worne, Rte. 73, Lyton Industrial Park, Berlin, N.J. 08009

[21] Appl. No.: 568,768

[22] Filed: Apr. 16, 1975

[51] Int. Cl.² .......................... C02C 1/14; A23K 1/12
[52] U.S. Cl. .................................. 426/59; 426/31; 426/52; 426/53; 426/54; 426/55; 195/4; 195/28 R
[58] Field of Search ........................ 426/49, 52, 53, 54, 426/55, 59, 31, 56; 195/4, 28 R, 29

[56] References Cited

U.S. PATENT DOCUMENTS

| | | | |
|---|---|---|---|
| 3,462,275 | 8/1969 | Bellamy | 426/53 |
| 3,546,812 | 12/1970 | Kobayashi et al. | 426/53 X |
| 3,633,547 | 1/1972 | Stevens et al. | 426/54 |
| 3,711,392 | 1/1973 | Metzger | 204/180 R |
| 3,773,659 | 11/1973 | Carlson et al. | 210/11 X |
| 3,838,198 | 9/1974 | Bellamy et al. | 426/53 |
| 3,846,558 | 11/1974 | Stevens | 426/59 X |

*Primary Examiner*—Raymond N. Jones
*Assistant Examiner*—Esther M. Kepplinger
*Attorney, Agent, or Firm*—Townsend and Townsend

[57] ABSTRACT

A five-step manufacturing method using broad spectrum hydrolytic enzymes to decompose the volatile fraction of organic waste materials into lower molecular weight, intermediate substrate nutrients to be consumed in turn by selected microorganisms to produce a cellular biomass of microbial cells subsequently harvested for use as a bio-protein feed supplement for farm and domestic animals. A wide range of agricultural, industrial and organic waste materials may be used as the input raw material resource for biochemical processing to bio-protein feed. Applied to the use of cattle manure slurry as raw materials, the biolytic decomposition step employs hydrolyzing enzymes to dismutate volatile organic insoluble high molecular weight proteins, starches, fats, and partially hydrolyzed cellulose compounds into soluble, low molecular weight nutrient intermediates in solution, from which the relatively stable cellulose-lignin solid by-product fraction is separated and dewatered. The Cellular Synthesis step uses selected microorganisms which metabolize and convert these nutrient intermediate products, plus oxygen and nitrogen from air, in their growth and proliferation into a biomass of microbial cells. The biomass is separated and utilized as a single cell bio-protein feed supplement for farm animals. The remaining liquid fraction, mainly water and relatively stable organic matter and mineral salts in solution, may be stored for subsequent irrigation and conditioning of agricultural lands and in the interim may be recirculated for feedlot flushing. The solids by-product, mainly cellulose and lignin, may be used as a fuel or biochemical feedstock or may be recombined with the liquid fraction during irrigation discharge to add mulch-fertilizer soil building values.

13 Claims, 1 Drawing Figure

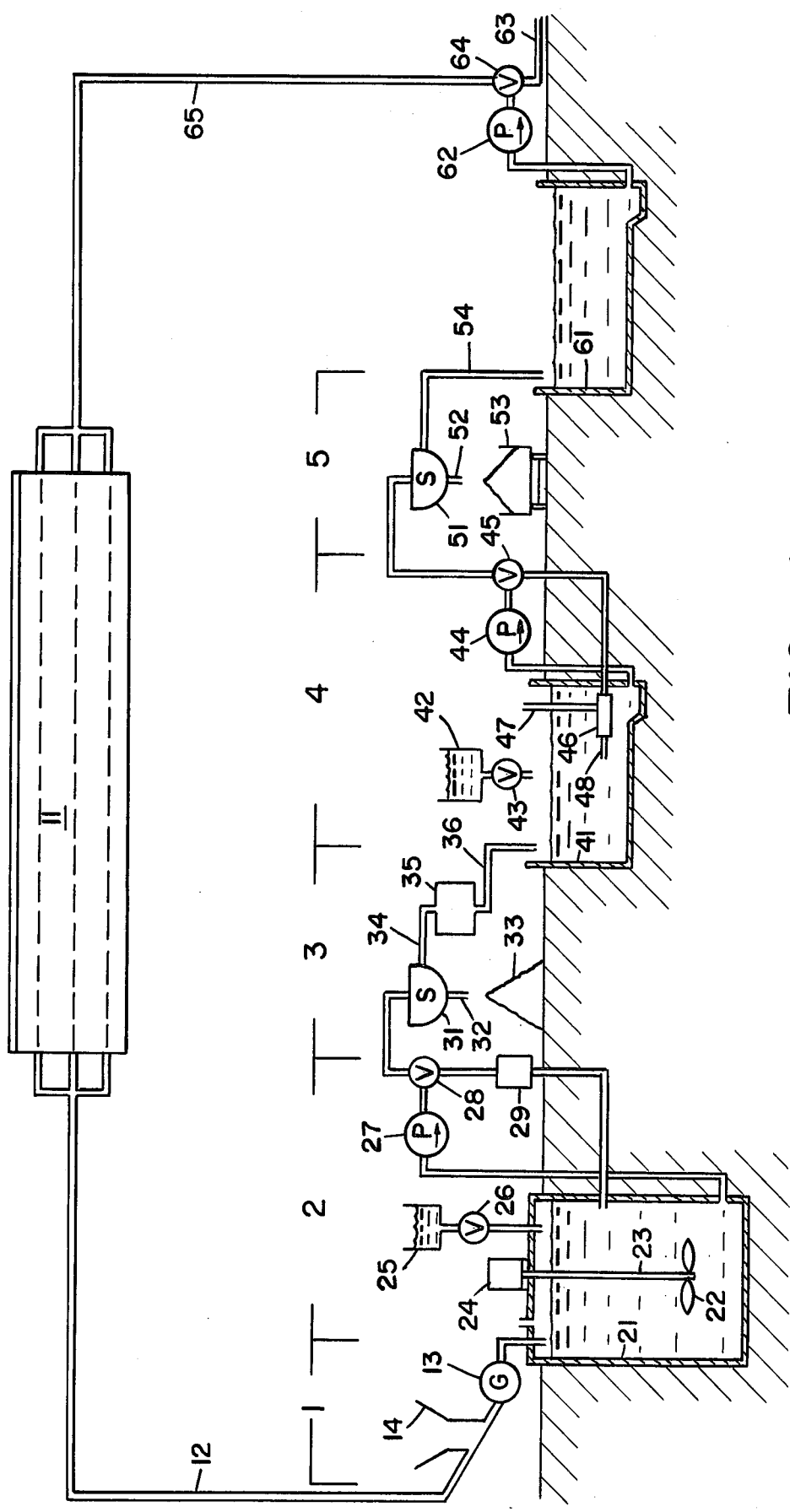
FIG_1

BIO-PROTEIN FEED MANUFACTURING METHOD

BACKGROUND OF THE INVENTION

The February 1974 Staff Report of the National Industrial Pollution Control Council (U.S. Government Printing Office 1971, 431-795/200) on the subject of "Animal Wastes" summarized the growing problem of pollution of water, soil and air resources created by the waste products of farm animals. A major source of environmental pollution is the excreted waste products of farm animals in feedlots, particularly beef cattle. More specific information has been published in "The Mounting Problem of Cattle Feedlot Pollution," Agricultural Science Review, U.S. Department of Agriculture, Volume 9, No. 1, 1971.

In a paper "A Systems Approach to Cattle Feedlot Pollution Control" presented at the May 1972 National Meeting of the American Institute of Chemical Engineers, St. Louis, Mo., Dr. Eugene Coleman analyzed the manure slurry discharged from a slotted floor confinement feedlot, in which the manure accumulates in subfloor pits cleaned out periodically by cable drawn scraper blades. The daily discharge from a feedlot with 10,000 head of average 800 pound cattle is a slurry containing about 45 tons (dry weight) of solids in about 70,000 gallons of water plus additional water from overflow of watering troughs and from rainstorm runoff. Each such 10,000 head feedlot module creates the quivalent of the sewage pollution potential of a city of 100,000 persons. Feedlot installations for 50,000 head or more are not unusual.

U.S. Pat. No. 3,859,962 granted to Ralph Kissinger, Jr., describes an improved flushable feedlot floor including multiple inclined floor slabs sloped to drain manure into subfloor slotted flumes which are cleaned by hydraulic flushing. In cold weather areas, such feedlots are usually flushed with manure liquid effluent recirculated from a storage lagoon which in turn is emptied occasionally for disposal on agricultural lands.

As regards energy and feed utilization, most cattle feeding operations are relatively inefficient. Typically each head of cattle consumes a daily ration of about 20 pounds of high quality feed, including highcost cereal grains plus about 5 gallons of water, to produce a daily marketable weight gain of about 2-½ pounds plus about 65 pounds of manure slurry. Much of the organic nutrient potential of the feed is not assimilated by the animals and is discharged as a partially digested biologically active manure slurry with major environmental pollution potentials if discharged to surface or subsurface waters, or if allowed to decompose and volatilize on exposure to sun and air. If stored in lagoons, anaerobic decomposition will convert the material to a relatively worthless sludge plus gases dissipated to the atmosphere.

Raw manures from farm animals are often used as fertilizer for distribution to agricultural lands. However, its value for direct use is limited by the fact that such material is only partly decomposed. In the soil, aerobic bacterial decomposition of the more volatile organic nutrients proceeds very rapidly and in this process the microorganisms utilize nitrogen that would otherwise be available for stimulation of fieldcrop growth. Such nutrients are returned to the soil eventually upon eventual decomposition of the manure; however, the short term fieldcrop growth results may be unsatisfactory.

In the co-pending patent application of Lennart G. Erickson and Wm. Scott Erickson, "Microorganic Fertilizer Manufacturing Method," Serial 528,070, there is described an improved biochemical method for use of the volatile organic fraction of farm animal manure as raw materials for manufacture of an improved liquid fertilizer. This continuous processing method for year-round production and distribution of liquid fertilizer is of limited utility in areas where extended periods of below freezing weather occur. The quantity of fertilizer produced is such that economical use of this method is restricted to situations where large areas of nearby agricultural lands are available for efficient utilization.

SUMMARY OF THE INVENTION AND OBJECTS

This invention provides for effective and economical use of volatile organic "waste" materials as the raw material resource for production of a high quality single cell bio-protein animal feed supplement plus secondary biochemically stabilized solid and liquid byproducts. Primary raw material "waste" resources are manure, solid and liquid, from feedlot cattle and other farm animals and fowl. Other agricultural, domestic and industrial organic waste materials may be used as input raw materials. The method of our invention comprises five specific steps, preferably carried out in sequence (all percentages given are by weight):

1. Grinding or shredding the input raw materials to coarse particulate size,
2. Biolytic Decomposition in a liquid solution containing a broad spectrum enzyme complex capable of hydrolyzing the insoluble high molecular weight proteins, starches, and fats into soluble low molecular weight intermediates,
3. Separation of Cellulose-lignin particulate solids as a byproduct; dewatered to less than 50% moisture content to inhibit biochemical decomposition during long term dry storage. Dewatering to this level is possible due to biochemical preconditioning during the Biolytic Decomposition step of our invention. Thus an increased proportion of nutrients in liquid form are released for subsequent processing.
4. Cellular Synthesis of the organic intermediate liquid nutrient substrate materials in aerated solution, inoculated with selected microorganisms to metabolize and resynthesize the intermediate nutrient substrate materials, plus oxygen and nitrogen from air, into cellular material. These cells are single cell bacteria which proliferate exponentially by growth and cell division into a biomass of cells limited only by availability of nutrients and air in solution.
5. Separation of Bio-protein cellular biomass, harvested for use as the primary animal feed product of this invention. This material in a dehydrated state is biologically stable, comprising 40 to 50 percent high grade protein and may be directly incorporated in either a dehydrated or hydrated state as a feed supplement for cattle or other farm or domestic animals.

The liquid residual byproduct remaining after the five step process of this invention is biologically stabilized, deodorized, and has a low Biological Oxygen Demand. It may be stored indefinitely in a pond for interim use as a hydraulic fluid for flush cleaning of animal feedlots and when needed may be distributed to agricultural lands as irrigation water. This water residual contains a residue of non-volatile organic materials in solution, of value as a fertilizer soil conditioning material.

The cellulose-lignin dry solids byproduct may be used for industrial purposes, or burned as a fuel, or may be recombined in solution during irrigation operations and recycled back to the land for its mulch-soilbuilding value.

An object of this invention is to employ hydrolytic enzymes to biochemically metabolize the volatile organic fraction of organic waste materials, and selected microorganisms to synthesize the resultant nutrient intermediates into a biomass of single cell proteinaceous material harvested for use as an animal feed supplement.

An object of this invention is to biolytically process the cellulose-lignin fraction of organic waste materials to allow effective separation from the more volatile organic fraction of such wastes and dewatering to moisture content levels below 50%, as necessary to inhibit bacterial decomposition during storage.

An object of this invention is to remove volatile organic nutrient materials and non-volatile organic nutrient solids from the input wastewaters, thus to produce a liquid byproduct which may be stored, recycled as a hydraulic flushing fluid and efficiently utilized for irrigation and soil conditioning values on relatively small areas of agricultural land.

An object of this invention is to provide a method useful under any climatic conditions for efficiently processing volatile organic wastes into stabilized solid, liquid, and synthesized nutrient fractions suitable for storage and use when convenient.

An object of this invention is to provide for conservation and efficient usage of the raw material and energy potentials of agricultural and other organic waste materials currently discarded, often with adverse effect upon the environment.

Referring to FIG. 1 there is shown schematically a flushable cattle confinement floor 11, as described in the referenced patent issued to Ralph Kissinger, Jr., providing a discharge flow of liquid manure slurry via pipeline 12 as the source of raw material to be processed according to the method of our invention. Daily discharge of manure slurry from each 1000 head of 800 pound cattle in such a facility is about 7,850 gallons weighing about 65,000 pounds. Of this about 86% is water and 8% is relatively stable organic material including cellulose and lignin and some mineral salts. The remaining approximately six percent of 3,900 pounds is composed of volatile organic solids, mostly insoluble proteins, starches, fat and partially hydrolyzed cellulose. These high vmolecular weight components in combination with water are retained as a viscous semi-solid mass. The resultant slurry has a viscous, gelatinous texture which prevents dewatering to less than 60 percent moisture content by conventional means such as high-pressure centrifugal or filtering devices. These volatile organic nutrient solids are normally subject to random decomposition by both aerobic and anaerobic bacteria and are subject to oxidation and vaporization upon exposure to warm air and sunlight. These reactions, if uncontrolled, tend to destroy the potential economic values of this material. The byproducts of such decomposition include noxious gases which are environmental pollutants and injurious to the health of the farm animals and personnnel.

The first step of our method involves grinding and shredding of the raw material, if necessary, into coarse particulate size by means of grinder 13. Such devices are well known in the art. The purpose of this operation is to reduce the raw material solids to resonably sized particles to facilitate attack by enzymes and to facilitate suspension in solution. Water may be added to adjust solids content to about 10–15%.

Our second step involves use of a vented biolytic tank 21 to receive the input raw material in solution, preferably in batch quantities to substantially fill the tank. Recirculation as necessary to maintain the particulate matter in suspension may be accomplished by means of a subsurface impeller 22 driven by shaft 23 and motor 24, or by other means well known in the art.

The biolytic decomposition process is initiated by addition from batch tank 25 and control valve 26 of a solution of broad spectrum hydrolyzing enzymes into tank 21. The enzymes used are composed of proteolytic, amylolytic, lipolytic and cellulolytic enzymes capable of hydrolyzing the high molecular weight substrates into low molecular weight intermediates.

The enzymes may either be prepared by growing selected organisms in media especially prepared for enzyme production, after which the organisms are separated and the enzyme broth is used to treat the substrate; or powdered, broad spectrum hydrolyzing enzymes may be dissolved in water and added to the biolytic tank 21. The amount of enzyme concentrate required for effective hydrolysis is about 1/10% by weight relative to the dry weight of volatile organic solids in solution. In addition, a biodegradable surface-active non-ionic wetting agent suited to reduction of surface and interfacial tension of water is added to a concentration of one part in 2500–5000 to aid in emulsification and subsequent biodegradation of fats and oils. The enzyme concentration is sufficient to hydrolyze and liquify the insoluble volatile organic material fraction within one to four hours. This material is mainly fine particulate organic matter, as compared to the relatively non-volatile fractions of celluloselignin components which decompose much more slowly.

The biolytic decomposition process requires a minimum fluid temperature of about 60° F. The reaction may be accelerated by warming the fluid contents of biolytic tank 21 to an optimum 100°–120° F. temperature range, but not higher than 140° F. This could be accomplished by recirculation through pump 27, valve 28, and heater 29, or by means of an immersion heater. If internal combustion engines are used in the related installation, the resultant waste heat could be utilized for warming the contents of biolytic tank 21. Additionally, the tank could be constructed of thermal insulating material and may be covered. The biolytic decomposition process can also be accelerated if necessary by addition of buffering chemicals to adjust the solution pH value to optimum for the specific enzymes employed.

Our third step involves mechanical separation and dewatering of the non-volatile solids fraction of the raw material remaining in biolytic tank 21. This comprises mainly cellulose and lignin materials partially decomposed by action of the hydrolytic enzymes of step two upon the hemi-cellulose and other volatile nutrients bound within the cellular structure of such cellulose-lignin materials in the raw state. As a result of such biolytic preconditioning the contained water will be more completely released, for instance, by means of centrifugal separator 31 into which the fluidized contents of tank 21 are discharged through pump 27 and two-way valve 28 rotated 90 degrees clockwise. The solids byproduct is discharged via pipe 32 to storage pile 33 with a moisture content less than 50%, low enough to substantially inhibit biochemical decomposition. If necessary, a small amount of lactic acid or other edible acid may be added to more completely reduce biochemical decomposition. This material may be held indefinitely in dry covered storage without appreciable deterioration. Without such biolytic preconditioning a moisture content of about 60% would remain after conventional dewatering operations and the material would be subject to continuing biochemical decomposition and deterioration if held in storage.

The liquid discharged from primary separator device 31 through pipe 34 may optionally be passed through a secondary separator 35 to remove fine particulate matter larger than about 10 microns in diameter. The liquid discharged via pie 36 into synthesis tank 41 contains practically all of the metabolite products of the biolytic process of step two in the form of soluble low molecular weight intermediates diffused in water. This nutrient solution provides the nutrient substrate materials for feeding the endogeneous synthesizing microorganisms employed in the fourth step Cellular Synthesis process of our invention.

Such cell synthesizing microorganisms are typically .35–10 microns in diameter. They feed selectively upon the lysed and partially degraded intermediates from the metobolic activities of the hydrolytic enzymes of Biolytic Decomposition, step two of our method. As they are limited by nature to single cell configurations, they proliferate by cellular growth and division, typical of bacterial microorgansims. Each cell divides approximately every 25–60 minutes and this exponential growth rate results in an indicated biomass proliferation in the range of 1,000 to 1,000,000 times in ten hours. In practice, ultimate growth is limited by depletion of available balanced nutrients and air and the inhibiting effect of cell metabolic wastes in solution.

The production and harvesting of the resultant biomass of single cell microorganisms may be regarded as sort of a hydroponic farming operation in an aerated liquid media. Analysis reveals that the dehydrated biomass cells comprise about 95% solids of which about half is high quality balanced food grade proteins well suited for use as an animal feed supplement. The remaining solids are mostly carbohydrates and small quantities of mineral salts. The cellular protoplasm is rich in active enzymes. The remarkably consistent food component analysis of this Microorganic Feed product is a reflection of the ability of these microorganisms to discriminate and select, from available nutrients in solution, the specific materials necessary for their growth and to reject excess materials in an unbalanced nutritional environment. In this respect they function with all the discrimination of plants of specific species.

About 15% of the nitrogen required in the metabolic process of cell synthesis is obtained by the microorganisms out of air in solution, the remainder being derived out of the nutrient substrate materials. This elemental nitrogen is synthesized and fixed by the microorganisms in the form of cellular protein and represents an important contribution to the values added by the method of our invention.

Our fourth step, cellular synthesis process, is initiated by addition from batch tank 42 through control valve 43 of an inoculating solution of synthesizing microorganisms into tank 41. If a liquid culture inoculum of heterotropic aerobic cell synthesizing microorganisms is used, the culture is grown to a concentration of ten million microorganisms per milliliter and added, in the proportion of about 5% by volume into the nutrient substrate solution in tank 41. If a dried culture is used, it is dispersed in water in the proportion of one pound per 25 gallons two hours prior to inoculum addition into cell synthesis tank 41 in the proportion of one pound of crude, dried microorganisms per thousand pounds of intermediate nutrient substrate in solution as a result of prior processing.

A large amount of air in solution is necessary for optimum metabolism of the synthesizing microorganisms. Pump 44 is used to recirculate the solution through valve 45 and an air aspirating device 46, receiving air through inlet tube 47 and discharging a jet of air-saturated water through nozzle 48 to maintain fluid aeration and circulation. Other fluid aeration methods well known in the art may be used including air infusion through subsurface perforated pipes, surface turbine air and water pumps and subsurface rotating mixers with vaned arms in which jets are provided for air infusion. If necessary, chemical buffering agents may be added to maintain a desirable pH value of about 6.8–7.2. Fluid heaters may be employed if necessary to supplement the substantial amount of heat generated by metabolic activity of the microorganism. Desirable temperature range is 80–95° F.

In the very favorable aerated recirculating fluid nutrient environment of synthesis tank 41, the synthesizing microorganisms will grow and multiply exponentially by cell division until the available nutrient intermediate substrate material is substantially consumed, usually in about six hours. During this time about 75–80% of the intermediate nutrient substrate materials in solution are utilized in growth and synthesis of a biomass of microbial cells. A proportion of the cells will die at this point; however, this does not reduce their value for subsequent harvest and use as a feed supplement. However, this harvesting operation should be completed promptly at this point to prevent subsequent deterioration of these cells by the process of endogeneous enzymatic autolysis.

Our fifth step involves mechanical separation and dewatering of the biomass of cells grown and synthesized in synthesis tank 41. A bowl-type centrifugal separator 51 may be used into which the fluidized contents of tank 41 are discharged through pump 44 and two-way valve 45, rotated 90° clockwise.

The bioprotein cellular material thus separated is discharged via pipe 52 to container 53 with a moisture content of about 45%, most of which is intracellular protoplasm fluid. A relatively clean final product is obtained in this fifth step separation process for the reason that most particulate solids remaining after our second step biolytic process have previously been removed in our third step separation process. Thus the intermediate nutrient solution supplied to synthesis tank 41 is practically free of particulate matter and the function of separation device 51 can be specifically adapted to separation of the biomass of cells grown and synthesized out of the inoculated solution of our fourth step cellular bioprotein production operation.

A small amount of lactic acid or other edible acid may be added to acidify the non-contained water, so as to suspend further biochemical activity while in storage. If the product is to be stored for any extended period of time, air should be restricted, usually by packaging in plastic bags. If required, the product may be pasteurized by heating for 5-10 minutes at a temperature of 180° F, or sterilized by exposure to ozone or by other techniques well known in the art. This product may be utilized on-site to replace otherwise costly protein feed supplements usually required in cattle feeding rations, or may be marketed as a commodity for use as a high protein component in farm or domestic animal feeds or for feeding fowl or fish.

The liquid residual byproduct discharged via pipe 54 into tank or pond 61 is biologically stabilized in that practically all volatile organic nutrients and organic solids have been removed by prior processing according to the method of our invention. It is virtually odorless and may be accumulated and stored indefinitely until needed, or discharged to surface or subsurface waters with minimal environmental impact. However, this liquid byproduct does contain in solution a substantial proportion of the non-volatile organic matter, present in the original input flow of wastewater. This material is useful up to heavy concentrations for soil building purposes. However, as most of the original content of nitrogen has been removed by prior processing, the liquid byproduct has little value as fertilizer and may be utilized as the economic equivalent of irrigation water. Thus the liquid byproduct of the method of our invention may be efficiently utilized on relatively small areas of agricultural land in any climate for a wide range of agricultural crops and in any climatic situation wherein occasional irrigation is advantageous. FIG. 1 illustrates a pump 62 and discharge pipeline 63 for use when the liquid by-product accumulated in tank or pond 61 is to be discharged, in which case two-way valve 64 is rotated 90 degrees counterclockwise.

The cellulose-lignin dry solids byproduct may be recycled back to the land for its mulch soilbuilding values. This can be accomplished by spreading or by recombining this material in solution in the liquid byproduct prior to recycling back to agricultural lands for irrigation and soilbuilding purposes. Alternatively, as this dewatered material is relatively free of volatile organic material, it may be useful for the following purposes:

Fuel for heating biolytic tank 21 or cell synthesis tank 61;

Mulch material for gardening or hydraulic reseeding of barren soil areas;

Cellulose--clean substrate raw material for further processing according to known techniques for enzymatic hydrolysis of cellulose into chemical feedstock intermediates.

Referring again to FIG. 1, which schematically illustrates a typical application utilizing the liquid manure discharge from a cattle feedlot as the source of organic raw material, the liquid byproduct may be recirculated via pump 62, two-way valve 64 and pipeline 65 back to the feedlot 11 for use in flush removal and hydraulic transpot of manure accumulations. This is advantageous for water conservation purposes and to minimize the accumulation of liquid that must be sotred during winter months in cold weather areas. Furthermore, as the liquid by-product is biochemically stable, the flushing operaion does not create the odor pollution often apparent when raw manure effluent is used for such recycle flushing operations.

For illustrative purposes we have elected to describe a typical application using the raw manure discharge from a cattle confinement feedlot as the input raw organic material resource for the method and practice of our invention. Alternatively, other types of organic waste materials, or combinations of such materials may be utilized as the input raw material resource. FIG. 1 illustrates hopper 14 as one means for input of alternative organic raw materials to be comminuted by grinder 13 and added into biolytic tank 21, with makeup water if necessary, to achieve a desirable raw solids content of about 10-15%. Suitable alternative sources of organic raw materials include:

Dry manure residues from conventional open type cattle feedlots;

Manure and bedding straw wastes from dairy cattle installations;

Manure from other farm animal feeding operations--pigs, chickens, turkeys, etc.;

Agricultural wastes, fieldcrop residues, bagasse, etc.;

Fruit and vegetable packinghouse wastes;

Animal packinghouse wastes and animal carcasses;

Forest treecrop residues, chips and sawdust;

Municipal sewage concentrates.

To facilitate the description of our five step process we have elected to illustrate in FIG. 1 a straight line batch flow for conversion of the input raw material slurry into the cellulose, bio-protein and liquid products of this invention. In the batch type operation described the various pumping and separating operations are completed sequentially, each in a matter of hours. Alternative pipe and valve arrangements may be used so that one set of pump and separator equipment could be used economically for all operations. For installations involving very large flow rates, continuous flow straight line processing arrangements may be utilized, as is well known in the art. Some types of raw material inputs may not require the comminution-grinding step 1 described above. It should be understood that this step is optional and may be omitted without departing from the essence of the method of our invention.

Although the foregoing improved method for manufacture of bio-protein feed has been described in some detail by way of illustration and example for purposes of clarity and understanding, it is to be understood that certain changes, modifications, and omissions may be practiced within the spirit of the invention as limited only by the scope of the appended claims.

What is claimed is:

1. A method for manufacturing a bioprotein animal feed supplement comprising: providing a slurry of raw organic waste containing biochemically volatile and biochemically non-volatile components, converting said biochemically volatile component to water soluble lower molecular weight intermediates essentially by the addition of organism-free hydrolyzing enzymes to said raw organic waste slurry at a temperature of about 60°-140° F, then separating said soluble lower molecular weight intermediates from biiochemically non-volatile solids in said waste solution, thereafter combining the separated lower molecular weight intermediates with cell synthesizing microorganisms substantially only under aerobic conditions permitting the microorganisms to feed upon said soluble lower molecular weight intermediates and thereby grow to produce a biomass of single cell microorganisms, and recovering said biomass of cells in a form suitable for use as an animal feed supplement.

2. A method in accordance with claim 1 wherein said organic waste comprises farm animal manure.

3. A method in accordance with claim 1 wherein said solution containing said hydrolyzing enzymes is maintained at a temperature of about 100°–120° F.

4. A method in accordance with claim 1 wherein said solution containing said synthesizing microorganisms is aerated substantially throughout the growth of said biomass.

5. A method in accordance with claim 1 wherein said combined lower molecular weight intermediates and cell synthesizing microorganisms are maintained in solution at a pH of about 6.8 to 7.2 and at a temperature of about 80°–95° F.

6. A method for manufacturing a bioprotein animal feed supplement comprising: collecting the manure waste in a cattle confinement feedlot, reducing the particle size of the collected manure, adding organism-free broad spectrum hydrolyzing enzymes to said manure in an aqueous media and hydrolyzing the protein therein to soluble lower molecular weight intermediates substantially only by the action of said enzymes at a temperature of about 60°–140° F, then separating the soluble lower molecular weight intermediates from non-soluble lower molecular weight intermediates from non-soluble solids, thereafter combining the soluble lower molecular weight intermediates with cell synthesizing microorganisms in a solution substantially only under aerobic conditions for causing the microorganisms to grow and produce a biomass of single cell microorganisms, and separating said biomass of microorganisms from the remainder of the solution within which it is grown for use as a feed supplement.

7. A method in accordance with claim 6 in which said biomass of microorganisms is mechanically separated from sufficient of its growth solution so as to yield about 40–50% protein content.

8. A method in accordance with claim 7 and including the addition of sufficient edible acid to said biomass to biochemically stabilize it.

9. A method in accordance with claim 6 in which said collected manure waste is combined with sufficient water to make a solids content of about 10–15%.

10. A method in accordance with claim 6 including the step of recycling the remaining liquid portion of the growth solution for use in hydraulically removing and transporting additional manure from said feed lot for processing into a feed supplement.

11. A method in accordance with claim 6 and including the step of mechanically de-watering said non-soluble solids after separation from said soluble lower molecular weight intermediates to a water content of less than 50% by weight.

12. A method in accordance with claim 1 wherein said organic waste is cattle manure.

13. A method in accordance with claim 12 wherein the nonvolatile solids separated from said soluble lower molecular weight intermediates is mechanically de-watered to a water content of less than about 50 percent to inhibit biochemical decomposition.

* * * * *